United States Patent
Ok et al.

(10) Patent No.: US 7,209,237 B2
(45) Date of Patent: Apr. 24, 2007

(54) OPTICAL SYSTEM FOR ANALYZING MULTI-CHANNEL SAMPLES AND MULTI-CHANNEL SAMPLE ANALYZER EMPLOYING THE SAME

(75) Inventors: Gyeong-sik Ok, Busan-si (KR); Yoon-kyoung Cho, Gyeonggi-do (KR); Jin-tae Kim, Gyeonggi-do (KR); Kwang-wook Oh, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 29 days.

(21) Appl. No.: 11/227,385

(22) Filed: Sep. 15, 2005

(65) Prior Publication Data

US 2006/0066857 A1    Mar. 30, 2006

(30) Foreign Application Priority Data

Sep. 16, 2004    (KR) .................. 10-2004-0074193

(51) Int. Cl.
*G01N 21/25* (2006.01)

(52) U.S. Cl. ........................................ 356/417
(58) Field of Classification Search ................. 356/417
See application file for complete search history.

(56) References Cited

U.S. PATENT DOCUMENTS

| | | | | |
|---|---|---|---|---|
| 4,601,576 A | * | 7/1986 | Galbraith | 356/237.3 |
| 4,692,024 A | * | 9/1987 | Bloss | 356/135 |
| 4,815,858 A | * | 3/1989 | Snail | 356/446 |
| 4,988,205 A | * | 1/1991 | Snail | 356/446 |
| 5,015,092 A | * | 5/1991 | Sting | 356/300 |
| 5,106,196 A | * | 4/1992 | Brierley | 356/445 |
| 6,369,893 B1 | | 4/2002 | Christel et al. | 356/417 |
| 6,414,311 B1 | * | 7/2002 | Wood et al. | 250/339.08 |
| 2003/0030817 A1 | * | 2/2003 | Lee et al. | 356/491 |
| 2003/0148505 A1 | | 8/2003 | Gambini et al. | 435/287.2 |

FOREIGN PATENT DOCUMENTS

JP    58-011838    1/1983

OTHER PUBLICATIONS

Korean Office Action (provided in Foreign and English translation) for Korean Application No. 10-2004-0074193; Dated: Mar. 27, 2006.

* cited by examiner

*Primary Examiner*—Gregory J. Toatley, Jr.
*Assistant Examiner*—Roy M. Punnoose
(74) *Attorney, Agent, or Firm*—Cantor Colburn LLP

(57) ABSTRACT

Provided are an optical system for analyzing multi-channel samples which uses a mirror rotating at high speeds and an aspherical mirror, and a multi-channel sample analyzer employing the optical system. The optical system for analyzing multi-channel samples, includes a light source unit which emits light traveling along an optical axis; a semi-spheroid aspherical mirror disposed in rotational symmetry about the optical axis; and an inclined mirror which reflects the light exiting the light source unit to the semi-spheroid aspherical mirror, while rotating about the optical axis, wherein an opening is formed in the center of the semi-spheroid aspherical mirror such that the light exiting the light source unit enters the inclined mirror through the semi-spheroid aspherical mirror.

19 Claims, 4 Drawing Sheets

OPTICAL SYSTEM FOR ANALYZING MULTI-CHANNEL SAMPLES AND MULTI-CHANNEL SAMPLE ANALYZER EMPLOYING THE SAME

BACKGROUND OF THE INVENTION

This application claims the benefit of Korean Patent Application No. 10-2004-0074193, filed on Sep. 16, 2004, in the Korean Intellectual Property Office, the disclosure of which is incorporated herein in its entirety by reference.

FIELD OF THE INVENTION

The present invention relates to an optical system for analyzing multi-channel samples and a multi-channel sample analyzer employing the same, and more particularly, to an optical system for analyzing multi-channel samples which uses a mirror rotating at high speeds and an aspherical mirror, and a multi-channel sample analyzer employing the optical system.

DESCRIPTION OF THE RELATED ART

A method of analyzing components or an absolute amount of a sample which includes irradiating a specific wavelength of light onto the sample and then detecting a spectrum of fluorescent light which is emitted from the sample is well known. For example, the respective bases of DNA can be labeled with fluorescent dyes having different emission wavelengths, and then, the spectrum of light emitted from the fluorescent dyes is analyzed, thereby identifying the base sequence of the DNA or confirming the absolute amount of the DNA.

FIG. 1 is a schematic view illustrating the structure of a conventional fluorescent analyzer 100. Referring to FIG. 1, the conventional fluorescent analyzer 100 generally includes a light source 110, filters 120 and 150, a dichroic mirror 140, an objective lens 145, a sample holder 130, and an optical detector 160, etc. The light source 110 may include various sources, such as a halogen lamp, a light-emitting diode (LED), a laser, etc. Light emitted from the light source 110 is transmitted through the first filter 120, thereby having a specific band of wavelength. Then, the light having a specific wavelength is reflected by the dichroic mirror 140 and enters a sample 170 on the sample holder 130. The fluorescent light emitted from the sample 170 is transmitted through the dichroic mirror 140 and the second filter 150 and detected by the optical detector 160. By analyzing the intensity of the fluorescent light emitted from the sample 170 by varying the wavelength property of the respective filters 120 and 150 or the light source 110, the components of the sample 170 can be identified.

Recently, to increase the efficiency of analyzing a sample and determine the identity of the sample at high speeds, a multi-channel sample analyzer, which can analyze a plurality of samples at once, has been developed. Multi-channel sample analysers can be roughly classified into apparatuses which determine a plurality of samples simultaneously using a plurality of detectors and apparatuses which determine a plurality of samples sequentially using a detector.

Examples of the apparatuses which determine a plurality of samples simultaneously using a plurality of detectors include one which uses a number of separate detectors equal to the number of the samples, and the detectors detect the fluorescent light emitted from the respective samples (Cepheid Smartcycler®; U.S. Pat. No. 6,369,893) and one in which a large area of light is irradiated onto a plurality of samples at once and a CCD having a large area detects the fluorescent lights emitted from the samples (ABI Prism 7000®; U.S. Patent Application No. 2003/0148505). However, in the former apparatus, the number of detector to be required is proportional to the number of sample, and thus, an increase of the number of sample (the number of detector in Cepheid Smartcycler®, which is commercially available, is 24) is limited. Furthermore, in the latter apparatus, the fluorescent lights emitted from different samples can be simultaneously detected by each detector, i.e., a cross-talk phenomenon of the fluorescent signals can occur. Thus, to overcome the phenomenon and increase the accuracy of the measurement, the apparatus has a complicated structure and a large size. Especially, the CCD having a large area which has a high accuracy required in fluorescent analysis is very expensive and a reduction of its size is technically limited.

The apparatus which measures a plurality of samples sequentially using a detector includes one which measures the samples placed on a large sample holder while scanning over the samples in XY-directions using the detector and one which measures the samples using a fixed detector while rapidly rotating a circular sample holder on which the samples are placed. In the former apparatus, since the detector cannot easily move above the samples at high speeds, there is a limit to a speed of measuring the samples. In addition, when there are too many samples to be detected, the detector must be able to scan over the large area, and thus, the apparatus has a very complicated structure and a large size. In the latter apparatus, since the samples rotate at high speeds under the fixed detector, the samples can be measured at relatively high speeds. However, when there is an excess of samples to be detected, the size of the sample holder must be increased, and to rotate the large sample holder at high speeds, the consumption of electric power greatly increases. Thus, a reduction of the size of the apparatus is limited.

SUMMARY OF THE INVENTION

The present invention provides a simple and small-sized portable optical system for analyzing multi-channel samples, which can measure a plurality of samples in real-time at high speeds.

The present invention also provides a multi-channel sample analyzer employing the above optical system.

According to an aspect of the present invention, there is provided an optical system for analyzing multi-channel samples, comprising: a light source unit which emits light traveling along an optical axis; a semi-spheroid aspherical mirror disposed in rotational symmetry about the optical axis; and an inclined mirror which reflects the light exiting the light source unit to the semi-spheroid aspherical mirror, while rotating about the optical axis, wherein an opening is formed in the center of the semi-spheroid aspherical mirror such that the light exiting the light source unit enters the inclined mirror through the semi-spheroid aspherical mirror.

The inclined mirror may be formed on one end of a cylindrical bar which rotates about the optical axis. A mirror surface of the semi-spheroid aspherical mirror may be disposed opposite to the light source unit and facing the inclined mirror. Especially, the semi-spheroid aspherical mirror has a reflection surface in an ellipsoidal shape which has a focal point on the sample in the direction of the optical axis and a focal point on the inclined mirror (at which the optical axis and the inclined mirror cross) in order to efficiently collect the fluorescent lights generated after radiating the excitation beam to the samples and has a circular mirror surface in cross-sectional direction perpendicular to the optical axis such that radiation for exciting the plurality of samples and the collection of the fluorescent signals generated due to the radiation can be sequentially performed.

According to another aspect of the present invention, there is provided a multi-channel sample analyzer comprising: a light source unit which emits light traveling along an optical axis; a semi-spheroid aspherical mirror disposed in rotational symmetry about the optical axis; an inclined mirror which reflects the light exiting the light source unit to the semi-spheroid aspherical mirror, while rotating about the optical axis; a sample holder disposed facing the semi-spheroid aspherical mirror such that the light reflected by the semi-spheroid aspherical mirror enters a plurality of samples on the sample holder; and a detector which detects the lights emitted from the samples.

The multi-channel sample analyzer may further comprise an objective lens disposed between the light source unit and the semi-spheroid aspherical mirror in order to collimate the light exiting the light source unit.

The multi-channel sample analyzer may further comprise a dichroic mirror which transmits the light exiting the light source unit to the inclined mirror and reflects the light emitted from the samples toward the detector.

The light source unit may comprise at least one light source, each light source emitting light having a wavelength different from each other; and at least one dichroic mirror, each dichroic mirror reflects the light emitted from the corresponding light source and transmits the light(s) emitted from the other light source(s) such that each of the lights emitted from the at least one light source can travel parallel to the optical axis.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the constitution and operation of an optical system for analyzing multi-channel samples and a multi-channel sample analyzer employing the optical system according to embodiments of the present invention will be described in more detail with reference to the attached drawings.

Figure 1:
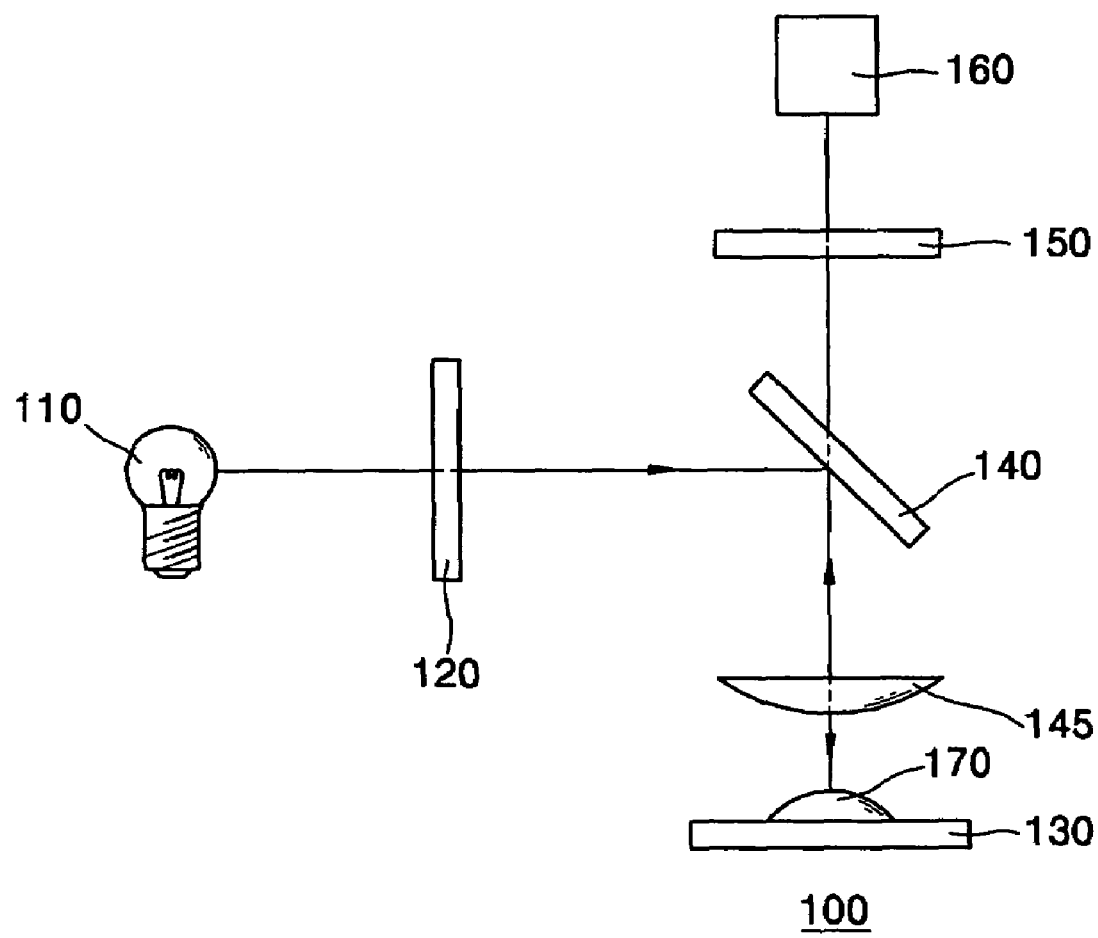
FIG. 1 is a schematic view illustrating the structure of a conventional fluorescence analyzer.
Figure 2:
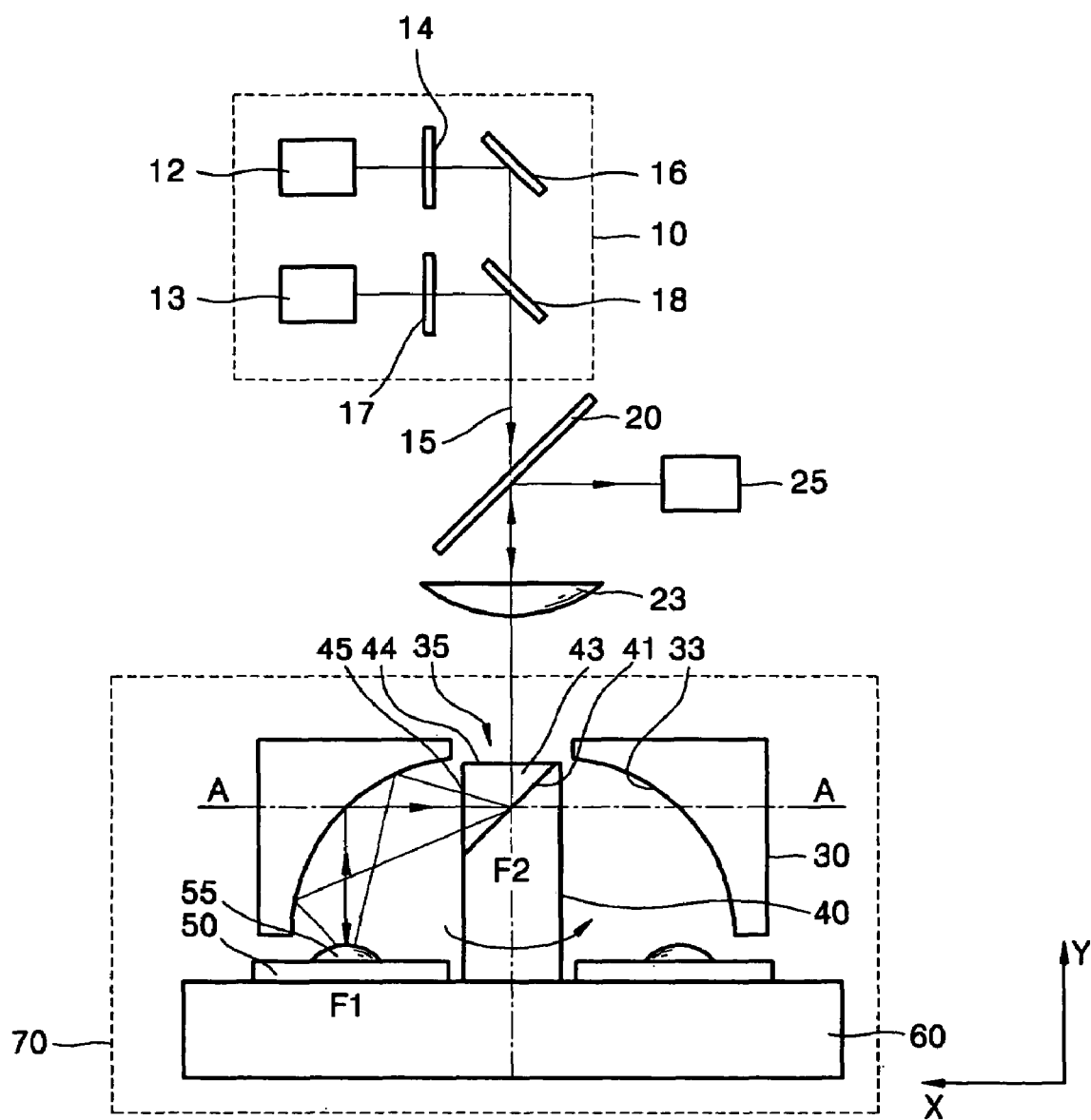
FIG. 2 is a schematic view illustrating the structures of an optical system for analyzing multi-channel samples and a multi-channel sample analyzer according to an embodiment of the present invention.

FIG. 2 is a schematic view illustrating the structures of the optical system for analyzing multi-channel samples and the multi-channel sample analyzer according to an embodiment of the present invention. As illustrated in FIG. 2, the multi-channel sample analyzer according to an embodiment of the present invention comprises a light source unit 10 which emits light traveling along an optical axis 15; a semi-spheroid aspherical mirror 30 disposed in rotational symmetry about the optical axis 15; an inclined mirror 41 which reflects the light exiting the light source unit 10 to the semi-spheroid aspherical mirror 30, while rotating about the optical axis 15; a sample holder 50 disposed facing the semi-spheroid aspherical mirror 30 such that the light reflected by the semi-spheroid aspherical mirror 30 enters a plurality of samples 55 on the sample holder 50; a detector 25 which detects the lights emitted from the samples 55; an objective lens 23 disposed between the light source unit 10 and the semi-spheroid aspherical mirror 30 in order to collimate the light exiting the light source unit 10; and a dichroic mirror 20 which transmits the light exiting the light source unit 10 to the inclined mirror 41 and reflects the light emitted from the samples 55 toward the detector 25.

The light source unit 10 comprises at least one light source 12 and 13, with each light source emitting light having a wavelength different from each other. Although FIG. 2 illustrates only two light sources 12 and 13, only one light source or at least three light sources can be used. The light sources 12 and 13 may include various sources, such as a halogen lamp, a light-emitting diode (LED), or laser etc. Filters 14 and 17 respectively filter the lights emitted from the light sources 12 and 13 such that each of the lights has a specific wavelength. As illustrated in FIG. 2, when at least two light sources 12 and 13 are used, dichroic mirrors 16 and 18 are required so that the light emitted from each of the light sources 12 and 13 travels parallel to the optical axis 15. Each of the dichroic mirrors 16 and 18 reflects the light emitted from the corresponding light source and transmits the light emitted from the other light source. For example, light having a first wavelength emitted from the first light source 12 is reflected by the first dichroic mirror 16 and transmitted through the second dichroic mirror 18 and travels parallel to the optical axis 15. Also, light having a second wavelength emitted from the second light source 13 is reflected by the second dichroic mirror 18 and travels parallel to the optical axis 15.

The light source unit 10, the dichroic mirror 20, the objective lens 23, and the detector 25, etc. are elements generally used in the conventional multi-channel sample analyzer and detailed descriptions on these elements will be omitted.

The characteristic portion of the multi-channel sample analyzer according to an embodiment of the present invention is the optical system 70 for analyzing multi-channel samples, which is disposed below the objective lens 23 in FIG. 2. As explained above, in case of using the conventional multi-channel sample analyzer which measures a plurality of samples using a fixed detector while rapidly rotating a circular sample holder on which the samples are placed, a plurality of samples can be measured at high speed. However, since the large sample holder is rotated, a reduction in the size of the analyzer is limited. To overcome this problem, the inventors have suggested the optical system 70 for analyzing multi-channel samples, which rotating the light to scan the samples, rather than rotating the sample holder. That is, the detector 25 and the sample holder 50 are fixed in position and the light exiting the light source unit 10 scans over the samples.

Figure 4:
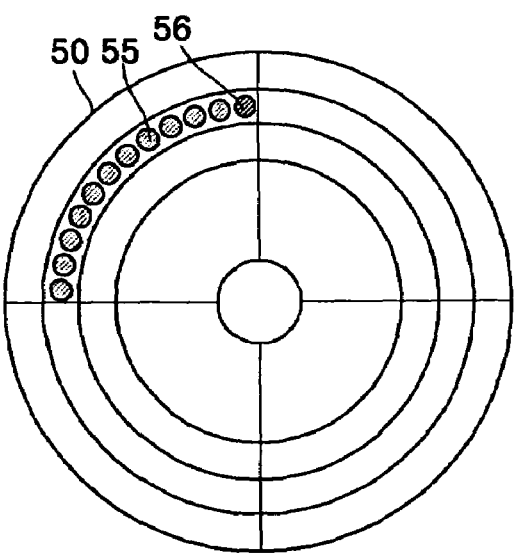
FIG. 4 is a view illustrating the arrangement of samples on a sample holder of a multi-channel sample analyzer according to an embodiment of the present invention.

As illustrated in FIG. 2, the optical system 70 for analyzing multi-channel samples according to an embodiment of the present invention comprises the semi-spheroid aspherical mirror 30 disposed in rotational symmetry about the optical axis 15 and the inclined mirror 41 which reflects the light exiting the light source unit 10 to the semi-spheroid aspherical mirror 30, while rotating about the optical axis 15. A mirror surface 33 of the semi-spheroid aspherical mirror 30 is disposed opposite to the light source unit 10 along a direction in which the light travels. That is, the mirror surface 33 of the semi-spheroid aspherical mirror 30 faces the inclined mirror 41. An opening is formed in the center of the semi-spheroid aspherical mirror 30 such that the light exiting the light source unit 10 enters the inclined mirror 41 through the semi-spheroid aspherical mirror 30. In the above structure, when the inclined mirror 41 rotates about the optical axis 15 at high speeds, an exit direction of the light entering the inclined mirror 41 varies along an azimuthal direction. Thus, as illustrated in FIG. 4 showing the arrangement of the samples 55 on the sample holder 50, the light reflected by the semi-spheroid aspherical mirror 30 can scan over the plurality of the samples 55 which are disposed in a circular shape on the sample holder 50 at high speeds.

The inclined mirror 41 is formed inclined on one end of a cylindrical bar 40 which rotates about the optical axis 15, for example. The inclined mirror 41 can rotate by rotating the cylindrical bar 40. The cylindrical bar 40 may be, for example, installed on a substrate 60 which is equipped with a motor (not shown) and a driving circuit (not shown) therein. When the cylindrical bar 40 is cut to be inclined and the inclined mirror 41 is formed on the cut end, the entire shape of the cylindrical bar 40 having the inclined mirror 41 is asymmetric about the optical axis 15. As a result, the weight center of the cylindrical bar 40 is not present on the optical axis 15, and thus, the inclined mirror 41 may not rotate about the optical axis 15 during the rotation, thereby shaking. A transparent bar 43 is attached to a top surface of the inclined mirror 41 such that the cylindrical bar 40 has a symmetric mass distribution on the optical axis 15 to prevent the cylindrical bar 40 from shaking during the rotation. As illustrated in FIG. 2, the shapes of the cylindrical bar 40 and the transparent bar 43 have symmetry about the optical axis 15.

As illustrated in FIG. 2, the light exiting the light source unit 10 enters the transparent bar 43 parallel to its center axis and travels to the inclined mirror 41. Then, the light is reflected at point F2, at which the optical axis 15 and the inclined mirror 41 cross, and is then again reflected by the semi-spheroid aspherical mirror 30, and is finally collected to a first focus F1 of the ellipsoidal surface of the semi-spheroid aspherical mirror 30, the sample 55 being placed at the first focus F1. The fluorescent light radiated from the first focus F1 due to the excitation of the incident light has a beam distribution (its center axis is the same as the incident optical axis) having a funnel shape and travels along the same optical axis as the incident path. That is, the fluorescent light radiated from the first focus F1 is firstly reflected by the semi-spheroid aspherical mirror 30 and collected to a second focus F2 and is then again reflected by the second focus F2, and is finally collimated to the objective lens 23 disposed above. Thus, the cross-section of the semi-spheroid aspherical mirror 30, taken along the direction of the optical axis 15 (i.e., the y-axis direction) in FIG. 2 has a reflection surface in an ellipsoidal shape which has a focus point on the sample 55 (i.e., the first focus F1) and a focus point on the inclined mirror 41 at which the optical axis 15 and the inclined mirror 41 cross (i.e., the second focus F2).

Figure 3:
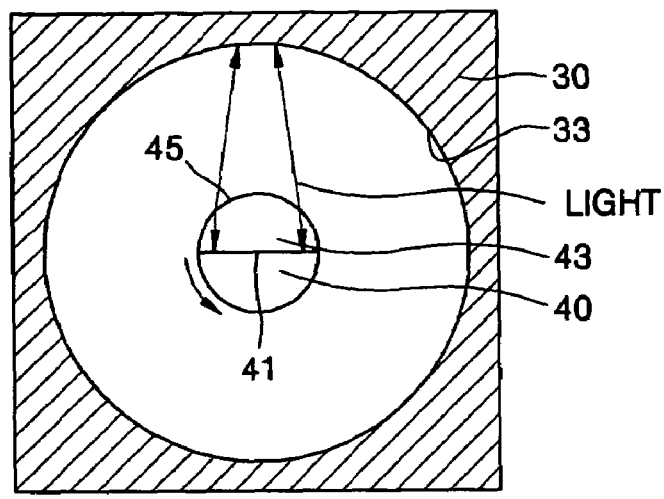
FIG. 3 is a cross-sectional view taken along line A—A of the optical system for analyzing multi-channel samples illustrated in FIG. 2.

FIG. 3 is a cross-sectional view taken along line A—A of the optical system for analyzing multi-channel samples illustrated in FIG. 2. As illustrated in FIG. 3, the cross-section of the semi-spheroid aspherical mirror 30, taken along the direction perpendicular to the optical axis 15 (i.e., the x-axis direction) has a circular shape which is rotationally symmetric, such that radiation for exciting the plurality of samples and the collection of the fluorescent signals generated due to the radiation can be sequentially scanned. Especially, a cross-section 45 of the transparent bar 43 has a cross-section of a cylindrical rod lens, i.e., a semi-circular shape. Thus, the light incident on the semi-spheroid aspherical mirror 30 after being reflected by the inclined mirror 41 is converged in the x-axis direction at the exit surface 45 of the transparent bar 43 without a change in the y-axis direction. In addition, the fluorescent light radiated from the surface of the sample 55 has a beam shape which is diverged from the first focus F1 on the surface of the sample 55 along the x-axis direction. However, since the semi-circular cross-section of the transparent bar 43 functions as a rod lens, the beam is converged and travels to the objective lens 23 disposed above.

The operation of the multi-channel sample analyzer using the above structure of the optical system is summarized as follows. The light exiting the light source unit 10 is transmitted through the dichroic mirror 20, the objective lens 23, and the transparent bar 43 and enters the inclined mirror 41. The light is reflected by the inclined mirror 41 and is then again reflected by the semi-spheroid aspherical mirror 30, and finally, enters the sample 55 on the sample holder 50. At this time, for example, the fluorescent material (not shown) contained in the sample 55 absorbs the incident light, thus being excited. The excited fluorescent material emits light different from the incident light. The light emitted from the fluorescent material in the sample 55 is reflected by the semi-spheroid aspherical mirror 30 and is then reflected by the inclined mirror 41 and travels to the dichroic mirror 20. In general, the light emitted from the fluorescent material in the sample 55 has a wavelength different from that of the light exiting the light source unit 10. Accordingly, the light traveling to the dichroic mirror 20 cannot be transmitted through the dichroic mirror 20 and is reflected by the dichroic mirror 20 toward the detector 25. During this process, the inclined mirror 41 rotates in an arrow direction, while reflecting the light exiting the light source unit 10 to a different sample. Thus, the plurality of samples 55 can be measured at high speeds by rotating only the inclined mirror 41, without rotating the detector 25 and the samples 55.

On the other hand, the plurality of samples 55 to be measured are disposed separated by a predetermined distance in a circular shape on the sample holder 50, as illustrated in FIG. 4. The radius of the circle can be varied according to the size or the number of the samples. A reference sample 56 which generates a mark signal is disposed at one of the positions of the samples 55 on the sample holder 50 such that the start of a revolution can be detected while the light scans over the samples 55 due to the rotation of the inclined mirror 41. For example, a fluorescent material which generates a signal sufficient to saturate the detector 25 is used as the reference sample 56.

Figure 5:
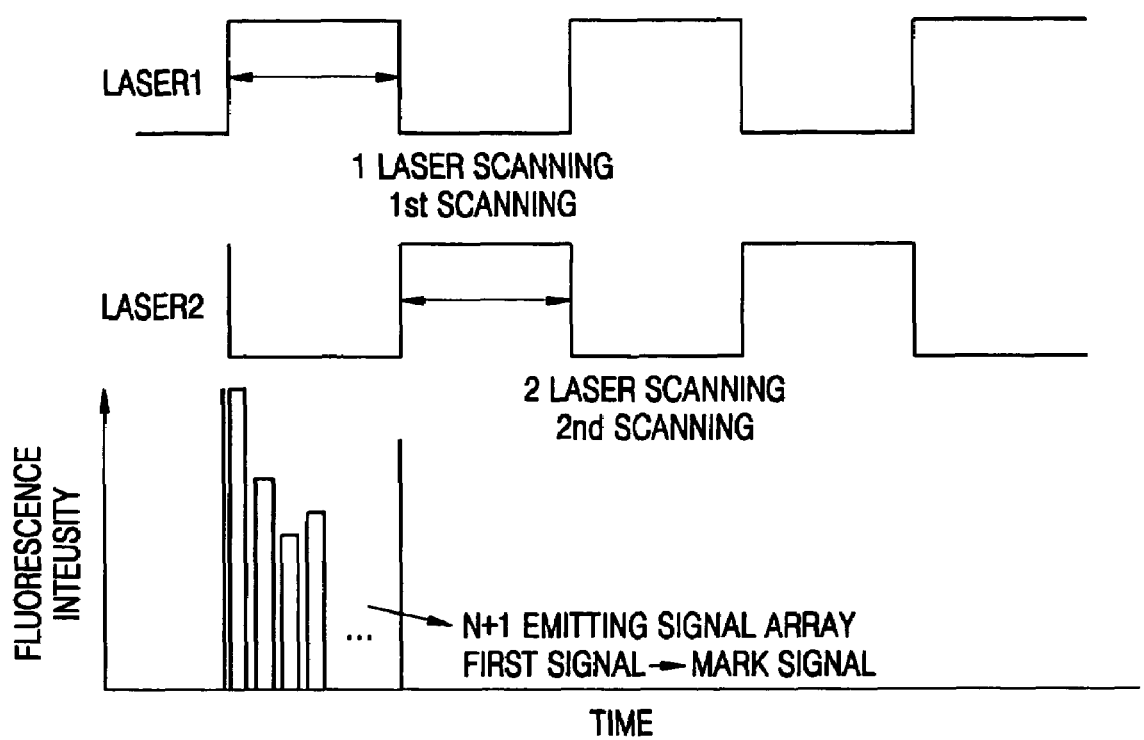
FIG. 5 is a timing view illustrating a signal processing mode of multi-channel samples.

As illustrated in FIG. 5, in a signal processing mode of the multi-channel sample analyzer, the light exiting the light source unit 10 is divided into a square wave which has a predetermined cycle by using a light chopper (not shown) or other electrical methods. For example, the lights exiting two light sources are timing controlled such that said lights are radiated sequentially while connected, for example, in the 1-2-1-2th light. The cycle of the square wave matches with the cycle of the rotation of the inclined mirror 41, such that the mark signal and the fluorescent signals from N samples (the total number of signals is N+1) can be detected for the first light source during the first rotation of the inclined mirror 41 and the mark signal and the fluorescent signals from N samples (the total number of signals is N+1) can be detected for the second light source during the second rotation of the inclined mirror 41.

Up to now, the optical system for analyzing multi-channel samples and the multi-channel sample analyzer employing the optical system according to embodiments of the present invention have been described in detail. According to the present invention, since the samples are detected in beam scanning using a mirror rotating at high speeds, a plurality of samples can be detected at high speeds while preventing an optical cross-talk between the samples.

In addition, according to the present invention, the plurality of samples can be detected by rotating only an inclined mirror. Thus, the structure of the optical system for analyzing multi-channel samples can be simplified and the components used can be minimized. As a result, the multi-channel sample analyzer according to the present invention can be reduced in size and produced at low costs.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An optical system for analyzing multi-channel samples, comprising:
    a light source unit which emits light traveling along an optical axis;
    a semi-spheroid aspherical mirror disposed in rotational symmetry about the optical axis; and
    an inclined mirror which reflects the light exiting the light source unit to the semi-spheroid aspherical mirror, while rotating about the optical axis,
    wherein an opening is formed in the center of the semi-spheroid aspherical mirror such that the light exiting the light source unit enters the inclined mirror through the semi-spheroid aspherical mirror.

2. The optical system of claim 1, wherein the inclined mirror is formed inclined on one end of a cylindrical bar which rotates about the optical axis.

3. The optical system of claim 2, wherein a transparent bar is attached to a top surface of the inclined mirror such that the cylindrical bar has a symmetric mass distribution on the optical axis to prevent the cylindrical bar from shaking during the rotation.

4. The optical system of claim 3, wherein an incident surface of the transparent bar is vertical to the light exiting the light source unit and an exit surface of the transparent bar has a shape of a cylindrical rod lens.

5. The optical system of claim 1, wherein a mirror surface of the semi-spheroid aspherical mirror is disposed opposite to the light source unit and facing the inclined mirror.

6. The optical system of claim 5, wherein a cross-section taken vertical to the optical axis of the semi-spheroid aspherical mirror has a circular shape and a cross-section taken along the optical axis of the semi-spheroid aspherical mirror has an ellipsoidal shape.

7. The optical system of claim 1, further comprising an objective lens disposed between the light source unit and the semi-spheroid aspherical mirror in order to collimate the light exiting the light source unit.

8. A multi-channel sample analyzer comprising:
    a light source unit which emits light traveling along an optical axis;
    a semi-spheroid aspherical mirror disposed in rotational symmetry about the optical axis;
    an inclined mirror which reflects the light exiting the light source unit to the semi-spheroid aspherical mirror, while rotating about the optical axis;
    a sample holder disposed facing the semi-spheroid aspherical mirror such that the light reflected by the semi-spheroid aspherical mirror enters a plurality of samples on the sample holder; and
    a detector which detects the lights emitted from the samples.

9. The multi-channel sample analyzer of claim 8, wherein the inclined mirror is formed inclined on one end of a cylindrical bar which rotates about the optical axis.

10. The multi-channel sample analyzer of claim 2, wherein a transparent bar is attached to a top surface of the inclined mirror such that the cylindrical bar has a symmetric mass distribution on the optical axis to prevent the cylindrical bar from shaking during the rotation.

11. The multi-channel sample analyzer of claim 10, wherein an incident surface of the transparent bar is vertical to the light exiting the light source unit and an exit surface of the transparent bar has a shape of a cylindrical rod lens.

12. The multi-channel sample analyzer of claim 8, wherein an opening is formed in the center of the semi-spheroid aspherical mirror such that the light exiting the light source unit enters the inclined mirror through the semi-spheroid aspherical mirror.

13. The multi-channel sample analyzer of claim 12, wherein a mirror surface of the semi-spheroid aspherical mirror is disposed opposite to the light source unit and facing the inclined mirror.

14. The multi-channel sample analyzer of claim 12, wherein a cross-section taken vertical to the optical axis of the semi-spheroid aspherical mirror has a circular shape and a cross-section taken along the optical axis of the semi-spheroid aspherical mirror has an ellipsoidal shape.

15. The multi-channel sample analyzer of claim 8, wherein the plurality of samples are disposed separated by a predetermined distance in a circular shape on a top surface of the sample holder.

16. The multi-channel sample analyzer of claim 8, further comprising an objective lens disposed between the light source unit and the semi-spheroid aspherical mirror in order to collimate the light exiting the light source unit.

17. The multi-channel sample analyzer of claim 8, further comprising a dichroic mirror which transmits the light exiting the light source unit to the inclined mirror and reflects the light emitted from the samples toward the detector.

18. The multi-channel sample analyzer of claim 8, wherein the light source unit comprises at least one light source, each light source emitting light having a wavelength different from each other; and
    at least one dichroic mirror, each dichroic mirror reflects the light emitted from the corresponding light source and transmits the light(s) emitted from the other light source(s) such that each of the lights emitted from the at least one light source can travel parallel to the optical axis.

19. The multi-channel sample analyzer of claim 18, wherein the light source unit further comprises at least one filter such that each of the lights emitted from the at least one light source has a specific wavelength.

* * * * *